United States Patent [19]
Mahiques et al.

[11] Patent Number: 6,140,371
[45] Date of Patent: Oct. 31, 2000

[54] THERAPEUTIC USES OF KNOWN ESTER AND AMIDE COMPOUNDS

[75] Inventors: Juan Carlos Mahiques; Ricardo Luis Elicabe; Raul Isidoro Koler; Ruben Martin Laguens; Enrique Leo Portiansky, all of La Plata (1900), Argentina

[73] Assignee: Medipharma S.A., La Plata, Argentina

[21] Appl. No.: 09/026,541

[22] Filed: Feb. 19, 1998

Related U.S. Application Data

[62] Division of application No. 08/527,503, Sep. 13, 1995, abandoned, which is a continuation of application No. 08/107,888, Aug. 18, 1993, abandoned.

[51] Int. Cl.$^7$ .................................................. A61K 31/16
[52] U.S. Cl. .................................................. 514/626
[58] Field of Search ............................................ 514/626

[56] References Cited

U.S. PATENT DOCUMENTS

| | | | |
|---|---|---|---|
| 4,181,725 | 1/1980 | Voorhees et al. | 424/288 |
| 4,757,088 | 7/1988 | Haines et al. | 514/563 |
| 5,331,013 | 7/1994 | Ahlman et al. | 514/626 |

OTHER PUBLICATIONS

Gundorova, R.A. et al, Oftal Mol. Zh. 1981, 36(3), 175–6, Abstract only.

Das et al, "Lidocaine: a hydroxyl radical scavenger and singlet oxygen quencher", *Mol. Cell.* Biochem. (Oct. 7, 1992), 115(2), 179–85.

Jarstrand et al, "Increased neutrophil radical production, increased lipid peroxidation and increased consumption of antioxidants in HIV–infected patients", *The Molecular Basis of Oxidative Damage by Leukocytes*, Eds A.J. Jesaitis and E.A. Dratz, CRC Press, Boca Raton, FL (1992), Meeting Date 1991, 321–3.

Kasavina, B.S. et al, Byull. Eksp. Biol. Med. (1982) 94(7), 27–8 (Abstract only).

Inozemtseva, L.I. Vestn. Akad. Med. Nauk SSSR (1991) (4):54–7 (Abstract only).

AN 1993:204760, Castilla et al, Rev. Argent. Microbiol, Jan. 1991.

AN 1988:179653, Tanaka et al, Virology, Jan. 1988.

AN 1988:400274, Bussereau et al, Acta Virol. (Engl. Ed.) (1988), 32(1), 33–49, Jan. 1988.

AN 1990:91623, Yanagi et al, Arch. Virol. (1989), 108 (1–2), 151–9, Jan. 1989.

AN 1990:240491, Minninger et al, Eur. Pat. Appl., 6, pp, Aug. 1989.

AN 1991:161608, Hirai et al, Biochim. Biophys. Acta (1991), 1088(2), 191–6, Jan. 1991.

Chemical Abstracts AN 1977:511486, Schaub et al, "reduction of ischemic myocardial damage in the dog by lidocaine infustion" Am. J. Pathol. (1977), 87(2), 399–414, Jan. 1977.

Chemical Abstracts AN 1995:256292, Palu et al, "Effects of herpes simples virus type 1 infection on the plasma membrane and related functions of HeLa S3 cells", J. Gen. Virol. (1994), 75(12), 3337–44, Jan. 1994.

*Primary Examiner*—Keith D. MacMillan
*Attorney, Agent, or Firm*—Morgan & Finnegan L.L.P.

[57] ABSTRACT

A number of new therapeutic uses have been found for compounds such as known local anesthetics which are quite different from the present therapeutic uses of these drugs. The uses include, for example; modulating lymphocytes, macrophages and other immune cell functions, or PMN functions; inhibiting the cytotoxic effect of polymorphonuclear neutrophils leucocytes; providing a protective effect on plasma cell membranes; and providing an antidote against intoxication by an intoxicants.

21 Claims, No Drawings

THERAPEUTIC USES OF KNOWN ESTER AND AMIDE COMPOUNDS

This is a divisional of application Ser. No. 08/527,503 filed Sep. 13, 1995, abandoned, which is a continuation of application Ser. No. 08/107,888, filed Aug. 18, 1993, abandoned.

FIELD OF THE INVENTION

The present invention relates to new therapeutic uses for known ester and amide type compounds.

BACKGROUND OF THE INVENTION

Various known drugs, including some which are local anesthetics, are synthetic products that can be considered as derivatives of a benzoic acid ester or amide and a tertiary amine having a hydrocarbon chain between these groups.

Thus, these molecule have 3 portions:

a) a lipophilic group, i.e., an arylic or aromatic moiety that includes an ester or amide group;

b) an hydrophilic group, the amine function; and c) an aliphatic moiety that connects both functions.

Local anesthetic drugs are capable of blocking nervous conductibility when administered locally. The simple direct contact of the drug with nerve tissue produces paralysis of the tissue.

There are various common types of local anesthesia including, for example:

1) topical or superficial, useful for mucoses;

2) intradermal or subcutaneous anesthesia;

3) regional anesthesia;

4) epidural anesthesia; and 5) rachidial or spinal anesthesy.

Those skilled in the art are normally familiar with this type of anesthesia.

Local anesthetic drugs can act by infiltration in the nerves. For acting by blocking the nervous conductibility, the drug must reach the nerve fibers penetrating the sheets that surround them. In this sense, the drug must be sufficiently hydrosoluble enough to diffuse among tissues and sufficiently liposoluble to penetrate across the lipidic layers of the membranes. In this way, the velocity of action of the drug depends upon its chemical nature, its concentration—a gradient is necessary—and of the type of nerve fiber, since in myelinated axons, the drug can only penetrate by the spaces corresponding to Ranvier nodes. Different diameter fibers offer more or less area to absorb the drug, which also modifies the velocity of action of the drug.

Local anesthetics are usually applied in the form of salts, specially as hydrochlorides. The salts are prepared by the combination of a strong acid with a weak alkali. Since they are acidic, with a pH of 4.0 to 6.0, they are highly soluble in water and highly ionized.

In contact with the alkalinity of the extracellular fluids, the tertiary amines are reformed and, since they are weakly alkaline and are poorly ionized, this part of the molecule can exert its effect.

The increasing of the pH of anesthetic drugs increase proportionally their potency, and it is convenient to increase this pH in those preparations used for topical use, since mucous membranes do not have an adequate buffer system to reform amines in the same manner as extracellular fluid.

The nervous stimulus runs along the nerve fiber by changing the polarity of the membrane, which originates a propagate potential. The local anesthetics, procaine and lidocaine, are capable of interrupting the nervous stimulus and this effect is due to a stabilization of the cell membrane that decreases the permeability of the cell membrane to sodium. Under normal conditions, sodium penetrates from the extracellular to the intracellular fluids to produce such a potential.

As is known, plasma cell membranes are comprised of a lipid bilayer covered by a hydrophilic protein layer, external and internally. Local anesthetics join themselves to the lipid bilayer by means of the lipophilic portion thereof and to the protein layer by means of the hydrophilic properties. In this way, the normal functions of the membrane are altered, disturbing the ionic exchange that normally occur.

These kinds of drugs can cause depression and/or stimulation of the central nervous system which is manifested as anxiety, tremor and convulsions, including those of the epileptoid type. These effects are directly proportional to the potency of the anesthetic.

The stimulation phenomena leads to depressive phenomena, in part due to fatigue of nervous centers and in part to a direct effect of the drug. This can lead to stupor, unconsciousness, areflexia and also death due to a bulbar respiratory center paralysis.

Experiments have demonstrated that procaine and lidocaine exert an anticholinergic effect manifested by blocking the cardioinhibitory effect of vagal stimulation. Lidocaine has been used as an antiarrythmia drug. In animals and human beings, high dosage can produce a reduction in cardiac contractility and hypotension.

Lidocaine, when administered in high dosage, can produce apnea by means of a bulbar respiratory center paralysis and also produces a marked reduction in cough reflex when is administered intravenously. It also has an antagonistic effect for acetylcholine, histamine and barium chlorhydride on bronchial smooth muscle fibers.

Anesthetic drugs, especially lidocaine, have a minor bacteriostatic and bactericidal effect directed to some kind of bacteria, such as Staphylococcus and *E. coli.*

None of the anesthetic agents are absorbed by intact skin. Instead, in injured skin, with removal of the corneal layer, absorption occurs, either with solutions or creams. In this case, maximal serum levels are achieved 6 to 10 minutes later.

Mucosal absorption differs among mucoses and is very fast in pharynx, tracheobronchial mucosa, lungs (aerosolization), conjunctiva and urethra and is low in bladder mucosa. There exist differences in mucosal absorption among the different drugs. i.e.: lidocaine is faster than other products such as procaine.

Oral route leads to low plasma levels, since the hepatic flow of blood drained from the gastrointestinal tract favors the quick degradation of the drug while parenteral routes lead to a fast absorption rate by a quick passage to blood stream. In accord with this, adrenaline is frequently added to retard the time of absortion and to extend the local effect. When absorbed, these drugs quickly reach the blood stream and are distributed in all tissues. The metabolism is different for each of the drugs of this pharmacological group.

Once procaine is absorbed, or when is administered intravenously, it is hydrolyzed by the enzyme pseudocholines-terase. This enzyme acts directly in blood plasma and in the liver, cleaving the drug to para-aminobenzoic acid and diethyl-aminoethanol. This cleavage is very fast (20 mg. per minute). The resulting products are excreted in urine. The half life of procaine is about 0.7 minutes.

With respect to other esteric local anesthetics, it can be said that pseudocholinesterase also cleaves them, but at a lower rate. i.e.: tetracaine is cleaved at a velocity about 5 times more slowly than procaine.

Since lidocaine is not an ester but rather is an amide, pseudocholinesterase cannot cleave it. Its cleavage is performed in the liver by means of oxidation, hydrolysis, des-ethylation and sulphoconjugation of the metabolites. The resulting metabolites are eliminated in the urine. Half life of lidocaine is about 20 minutes.

The pharmacokinetics of other amide anesthetics are not as well known as lidocaine, but in general terms, it is similar to that of the lidocaine. One of these amide products, prilocaine, when it is metabolized, produces a derivative, ortho-toluidine, which is responsible for the metahemoglobinemia observed when high dosage of prilocaine is administered.

Procaine and lidocaine have a low toxicity, and high dosages are required to produce signs and symptoms of intoxication. Up to 25 g of procaine were administered intravenously in one anesthetic therapy. In spite of this, sometimes, dosages of about 10 to 100 mg are sufficient enough to produce severe complications, attributed to idiosyncrasy of the drug. Toxic manifestations are nervous, cardiovascular or hematological.

Allergic reactions are not common and they consist in cutaneous manifestations, such as urticaria, angioneurotic edema, bronchospasm and, exceptionally, anaphylactic shock.

These drugs have few contraindications, since they do not affect parenchymatic tissues. The contraindications derive from the existence of hypersensitivity to the drug, but, in spite of this, they must be administered with special care in patients with myocardial disease, hepatic dysfunction and severe anemias.

Therapeutic uses of procaine and lidocaine administered by intravenous route include global anesthesia.

In some countries, procaine is used to produce a global anesthesia, administering it by intravenous route. This method is not dangerous: there was only one death in over more than 6200 patients treated with procaine (less than 0.01%).

Lidocaine hydrochloride is used in ventricular arrythmias.

Other uses of procaine include eutrophic and revitalizing effects.

Some years ago, procaine was used as a revitalizing and eutrophic agent. A series of 7,600 patients over 70 years old were treated with procaine, registering a good response, in the sense that they presented a better muscular tone, better hearing, and better intellectual functions. Another series of experiments in a similar group did not find modifications in the parameters measured. Today, it is believed that the use of procaine as a revitalizing and eutrophic agent is not justified.

The effects of lidocaine on cardiovascular system is similar to that of quinidine, and it is believed that its effect is due to its stabilizing property on plasma cell membranes.

Administration of lidocaine produces the following effects on myocardial cells:

a) depolarizing velocity of phase 0 is reduced;
b) conductibility velocity is reduced;
c) the action potential is slightly narrowed;
d) the automatism decays (phase 4);
e) cardiac excitability is reduced; and
f) the effective refractory period is smaller.

It must be said that ventricular fibers are more sensitive to lidocaine than auricular fibers.

Cardiac excitability is depressed by lidocaine (a negative bathmotropic effect), with a high electric stimulation threshold. The fibrillation threshold is also higher, so this drug is an antiarrhythmic agent. The ratio relative refractory period/ lasting of action potential is increased.

As a consequence of a decay of depolarizing velocity and of a reduction in the capability of response of the membrane, conductibility is reduced (a negative dromotropic effect).

High dosage of lidocaine can produce reduction of the auriculoventricular conductibility, with a longer lasting of the P-R interval and of the QRS complex.

Lidocaine has little or no effect on normal sinoauricular node, but the drug reduces the automatism of ectopic foci (a negative chronotropic effect).

Contractility is not affected by lidocaine, but high dosage administered intravenously can reduce contractility (a negative inotropic effect).

Lidocaine can effectively suppress ventricular extrasystolia and tachycardia, having minor effects on auricular extrasystolia, tachycardia and fibrillation.

Lidocaine produces, when is administered intravenously, a reduction in arterial tension. Since the drug does not reduce the hypertensive effect of adrenaline, but does reduce that of the nicotine, the hypotensive effect of lidocaine is due to a sympathetic ganglionar blocking.

Administered by oral route, only 35% of the amount of lidocaine is absorbed, and 60% of it is metabolized during the first passage through the liver. Administered by intramuscular route, absorption is efficient and 30 minutes later adequate plasma levels of lidocaine are found, lasting at least for 2 hours.

After intravenous injection, plasma levels of lidocaine decay quickly in two steps:

a) in the first step, a distribution of the drug in brain, heart, liver, kidney, skeletal muscle and adipose tissue is observed.

b) the second step consists in the metabolization of the drug in the liver and its excretion in urine.

The therapeutic plasma level of lidocaine is 0.2 to 0.5 mg/100 ml, and the toxic level is 0.7 to 0.9 mg/100 ml.

From blood lidocaine is retained in heart, brain, liver, kidney, skeletal muscle and adipose tissue, but 1 hour later, tissue levels are significantly reduced. This reduction is due to a fast metabolization in the liver. The metabolic derivatives and about 5 to 10% of the intact drug are excreted in urine. The half life of the drug is about 20 minutes.

SUMMARY OF THE INVENTION

The present invention relates to a number of new therapeutic uses of known compounds including known local anesthetics, such as, for example, lidocaine and procaine. The new uses are quite different from the present uses of these drugs.

DETAILED DESCRIPTION OF THE INVENTION

Based on the cell membrane stabilizing property of some known compounds including the local anesthetics which confers upon them their action on muscular and neuronal cells, a series of experiments were performed that demonstrates that these drugs exert substantially the same type of pharmacological action on cell membranes having cell types different from muscular and neuronal cells.

Among such cells, is polymorphonuclear neutrophils (PMNs) cells that mediate the cellular phase of the acute inflammatory response.

This type of leucocyte migrates to the site of where the acute response is produced and, at the site of inflammation, they tend to destroy the injurious noxes, by phagocytosis and/or by returning of lysosome enzyme to the extracellular fluid of lysosome enzymes. But, in this process, PMNs also destroy the tissue where the inflammation occurs, leading to a dysfunction of the tissue, which commonly produces clinical signs, depending on the magnitude of the inflammation and on the type of tissue injured.

In the present invention, experiments were performed in which mice infected with foot-and-mouth disease virus (FMDV) that developed an acute necrotizing pancreatitis are treated with a compound such as a local anesthetic. It was found that there was a marked diminished effect on necrosis and inflammatory exudate. It is known[1] that the compound such as the local anesthetic acts in stabilizing the PMN cell membrane, leading to an abolishment of the activation of these cells, and blocking the lysosomal enzyme release and/or blocking the phagocytosis process. Other mechanisms of action may possibly occur including that another mechanism is acting synergistically so as to provide protection of the injured cell that avoid its lysis.

[1] Peck, S. L.; Johnston, R. B. and Horwitz, L. D. Am. Soc. Pharm.Exp.Ther. 235:418–422, 1985.

In the instant experimental model, the absence of lytic effects on acinar cells of pretreated animals is in coincidence with the absence of leucocyte recruitment and low inflammatory response, observed in the control group, with high viral titers in pancreatic tissue, similar to the control group. While it may be postulated that the effect could be exerted on parenchymatic cells only, but experiments in which the drug is administered when the pancreatitis is already installed supports the idea that local anesthetic acts on the two cellular populations, PMNs and acinar cells. In support of this, other experiments have demonstrated that the local anesthetic reduces significantly pancreatic and hepatic injuries produced by acute intoxication with methanol.

On the other hand, in experiments in which an acute intoxication with other substances was produced, the administration of the local anesthetic reduced tissue damage, with low or no mortality of the animals as compared with the control groups. The last result supports the idea defined in the previous paragraph.

Experiments in which the number of granulomatous lesions of the liver caused by experimental infection of Histoplasma capsulatum in mice is reduced by administration of a local anesthetic, support the knowledge that local anesthetics also exert similar effects on macrophages[2] and lymphocytes[3], stabilizing the membranes of these cells and modulating their interactions.

[2] Cameron, D. J. Japan.J.Exp.Med. 56:265–269, 1986.

[3] Renzi-PM; Ginns-LC Immunopharmacol-Immunotoxicol 122417–37, 1990.

In another series of experiments of the present invention performed in order to know the effect of the drug on in vitro viral replication, it was observed that viral titers are reduced (1.5 or 2 logs) when the drug is administered prior to, or simultaneously with viral inoculation, but no significant reduction of viral titers is produced when the drug is administered after the viral adsorption takes place. These experiments apparently show that local anesthetics in some manner modify plasma cell membranes, possibly interfering with viral adsorption and/or denudation, exerting in this way an antiviral effect.

Also, experiments according to the present invention developed with human volunteers showed similar results, as they demonstrated the existence of significant modifications in the development and evolution of diverse inflammatory and immune diseases, of viral, bacterial or parasitic origin. Among them it can be cited diverse types of enteritis, hepatitis, herpes simplex infection and herpes zoster infection, all exemplified below.

Taking into account what is known about local anesthetics including the pharmacokinetics of these drugs and their absorption, local anesthetics can be administered to obtain the new activities found in the present invention by different routes, also in similar pathologies, depending of the type of pathology in study. It is clear that in enteric pathologies, it can be used by the oral or rectal routes. With the same criteria, herpetic lesions can be treated in a topical manner (solutions, creams, etc.) or the parenterally (subcutaneous, intramuscular-or intravenous). For example, herpetic eruptions of the genital or oral mucoses, or a ocular herpes infection can be treated topically alone association with a parenteral treatment.

Because of the drug effects of local anesthetics found in the present invention on different cellular systems, the drugs can be used as adjuvants in therapy with other pharmaceutical products, increasing the effectiveness of the pharmaceutical products, reducing dosage of the pharmaceutical products and/or reducing the time of administration of the specific pharmaceutical products.

In summary, the present invention has found that compounds such as known local anesthetics possess special protective effects on plasma cell membranes that avoids cellular damage, preventing in this way the deleterious action of diverse injuries, chemical or biological. This property makes this drug effective in the treatment of diverse diseases, already mentioned.

The present invention relates to the use of various compounds including local anesthetics in hitherto unknown functions. The local anesthetics include known compounds such as, for example, lidocaine hydrochloride (xylocaine), chloroprocaine hydrochloride, etidocaine hydrochloride, bupivacaine hydrochloride, mepivocaine hydrochloride, prilocaine hydrochloride, procaine hydrochloride, propoxycaine hydrochloride, tetracaine hydrochloride, benzocaine, dibucaine, and procainamide hydrochloride. It is contemplated that compounds which have minor structural modifications of the above-mentioned compounds which do not affect their therapeutic action fall with the scope of the compounds such as the local anesthetics for which new uses have been found in the instant invention.

Amongst the new uses which have been found in the present invention are: acute gastroenteropathies; chronic enteropathies; malabsorption syndrome caused by Giardia lamblia; acute hepatitis of diverse origin; acute pancreatitis of diverse origin; acute chemical intoxication; antidote for diverse intoxications; treatment of herpes simplex infection; treatment of herpes zoster infection; treatment of acquired immune deficiency syndrome, either viral or other etiology; treatment of diverse viral infections; in the treatment of vascular injuries in shock cases; as an adjuvant along with conventional therapies for the above-mentioned uses; as an adjuvant in the-process of postoperative recovery of major surgeries; as a prophylaxis in the immediate post-operative phase of major surgeries; in the known inhibition of the cytoxic effect of polymorphonuclear neutrophils leucocytes and the modulation of lymphocytes, macrophages and other immune cell functions as well as PMN functions; and as an adjuvant in the treatment of burn patients.

The local anesthetics are administered in the known formulation forms in non-toxic dosage concentrations sufficient to insure the release of sufficient dosage units of local anesthetic into the animal to provide the desired therapeutic effect. Specifically, the dosage amount contained in the present local anesthetic formulations is that amount needed to provide the new uses found in the present invention. The actual dosage amount administered can be determined by physical and physiological factors such as body weight, severity of condition, and idiopathy of the patient. With these considerations in mind, the dosage of the local anesthetic for a particular subject and of course of treatment can readily be determined.

The subjects to which the instant new uses apply include any animal in need of such treatment including human beings, other mammals, birds, amphibia and insects under culture (such as bees), and they must be considered equivalent for the purposes of the present invention and within the scope of the appended claims. In this patent, the terms, subject and animal are used interchangeably.

The following examples describe particular experiments performed with a local anesthetic on different animal models and on human volunteers, but are in no way intended to limit the scope of the present invention.

EXAMPLES

Example #1

Effect in Canine Acute Hemorrhagic Gastroenteritis Produced by Parvovirus Infection (Parvoviridae)

a.—Material and Methods

Thirty-two 3 to 6 months old male and female dogs of more than 3 kg of body weight, free of parasites and apparent disease were inoculated by peroral instillation with $10^7$, $TCI_{50}$ of canine parvovirus (CPV). Virus was obtained by clarification of feces from an animal with evident signs of CPV infection.

From the moment of the development of the first signs of disease, animals were grouped: one group (A) received 500 ml of saline solution by intravenous route with 5 ml of a 2% solution of lidocaine twice a day during 2 days. The other group (B) received only saline in a similar fashion.

Each 12 hours morbimortality was registered in the two groups, and 2 animals of each group were sacrificed, beginning at 12 hours after the appearance of signs and finishing at 60 hours for the group B (since at this time all animals died) and at 96 hours for the group A.

A complete necropsy was performed and samples of different organs were removed for morphological and virological studies. Surviving animals were bled 14 days later and serum was used to determine the presence of specific antibodies against CPV.

b.—Results

Morbimortality: all animals showed 3 to 7 days post-infection signs of disease, consisting in hyperthermia, weakness, asthenia, vomiting and bloody diarrhea.

Group B (control) showed a progressive evolution of the disease, all the animals died 60 hours after the signs of the disease began.

Group A (treated animals) showed a progressive recuperation since the second administration of the drug, registering no mortality among these animals. After 48 hours from the beginning of treatment, none of the animals showed signs of the disease.

Morphological study: animals of group B (control) showed lesions only in enteric mucosa and regional lymph nodes. Intestinal lesions consists of a massive necrosis of enteric villi, with indemnity of cripts in half of the animals, but without globet cells. The other half of animals showed a complete denudation of the mucosa. The inflammatory response was scarce or none. Lymph nodes showed a marked follicular hyperplasia with areas of necrosis.

Animals of group A (treated) showed lesions only at the enteric level, consisting of an acute inflammatory response that affected villous mucosa, with signs of epithelial regeneration from 2 to 4 hours post-treatment. Those animals sacrificed at 12 hours post-treatment showed necrosis similar to control group, but with inflammatory cells in villi. From this time, no necrosis was found and high mitotic activity was noticed lasting at least until 60 hours post-treatment. By 48 hours globet cells reappeared, and by 72 hours the mucosa presented a normal histological aspect.

Virological studies: virus could be recovered only from intestinal tract. Viral titers are expressed in Tables 1 and 2.

| Time | Control group (B) | Treated group (A) |
| --- | --- | --- |
| 12 hrs. | 20 | 0 |
| 24 hrs. | 20 | 16 |
| 36 hrs. | 40 | 320 |
| 48 hrs. | 40 | 320 |
| 60 hrs. | 40 | 160 |
| 72 hrs. | * | 40 |
| 84 hrs. |  | 40 |
| 96 hrs. |  | 40 |

*: from this time all animals died.

TABLE 1: Hemagglutinating Titers of Enteric Homogenates
Titers are expressed as the inverse of the last dilution which agglutinated sheep red cells.

| Time | Control group (B) | Treated group (A) |
| --- | --- | --- |
| 12 hrs. | $2.0 \times 10^{-4}$ | $2.1 \times 10^2$ |
| 24 hrs. | $2.8 \times 10^{-4}$ | $0.1 \times 10^4$ |
| 36 hrs. | $6.2 \times 10^{-4}$ | $0.5 \times 10^7$ |
| 48 hrs. | $7.4 \times 10^{-4}$ | $0.3 \times 10^7$ |
| 60 hrs. | $6.8 \times 10^{-4}$ | $2.3 \times 10^5$ |
| 72 hrs. | * | $6.3 \times 10^4$ |
| 84 hrs. |  | $5.8 \times 10^4$ |
| 96 hrs. |  | $6.0 \times 10^4$ |

*: from this time all animals died.

TABLE 2: Viral Titers of Enteric Homogenates
Titers are expressed as $TCID_{50}$/ml. Titers were obtained on Vero cells.

Serological study: surviving animals of group B (treated) showed 14 days post-treatment hemagglutination inhibiting antibodies in a titer of 640 and 20,480.

Conclusions: Lidocaine is highly effective in the treatment of canine acute hemorrhagic gastroenteritis produced by infection with CPV, since morbidity was reduced drastically and mortality was abolished.

Lidocaine modifies the morphological findings in bowel mucosa, indicating that necrosis is stopped and a significant recovery of the epithelia is taking place.

Lidocaine does not interfere with recognition of CPV antigens from immune system since high specific antibodies titers were found.

Example #2

Effect in Patients with Acute Hemorrhagic Diarrhea

Four patients with acute hemorraghic diarrhea of 3 days of evolution were treated twice a day for 2 days with lidocaine intravenously administered (5 ml of a 2% solution).

Results: After the second administration, all patients showed a significant recovery, with abolishment of symptomatology after 48 hours of treatment.

The number of fecal depositions progressively decreased, and the quality of feces was also modified. Two (2) of the 4 patients began to feed themselves with solid food in spite of the physician indications, at the second day of treatment, and they did not show any reactivation of their disease.

Rectoscopies were performed in all patients immediately before treatment, 2 and 7 days later. Two (2) of the patients accepted to be biopsed at the moment of the first and second rectoscopies.

Rectoscopy:

First one: One could observe multiple hemorrhagic petechia on a congestive mucosa with erosions of the surface and bloody mucous material in the walls of the rectum. This picture was similar in all the patients studied.

Second one: One could observe a congestive and edematous mucosa, without hemorrhages and erosions.

Third one: One could observe a normal mucosa.

Microscopic Examination of Mucosa:

First biopsy: Acute inflammatory process of mucosa with interstitial hemorrhages and epithelial erosion.

Second biopsy: Slight chronic inflammatory process with indemnity of epithelium. Morphological pictures were similar in both patients examined.

Conclusion: Lidocaine is effective in acute hemorrhagic diarrhea of diverse origin.

Example #3

Effects in a Patient with Ulcerative Colitis

Lidocaine was administered to a patient with an history of ulcerative colitis of 4 years evolution with the following schedule: 4 doses of lidocaine intravenously each 12 hours per week, during 4 weeks (5 ml, 2% solution).

During the treatment, diarrhea disappeared, and in the 5th week a fibrocolonoscopy was performed and a biopsy specimen was obtained.

The colonoscopy showed a congestive and edematous mucosa; no erosion could be observed.

In the microscopic examination, discrete foci of lymphocyte infiltrates in lamina propria with interstitial fibrosis could be observed, with absence of globet cells, hypotrophy of mucosa. The histopathological diagnosis was: quiescent ulcerative colitis.

Conclusions: Lidocaine seems to be an adequate treatment for ulcerative colitis.

Example #4

Effects in Patients with Malabsorption Syndrome Caused by Giardia Lamblia (Giardiasis)

Lidocaine was administered to two patients (5 ml, 2% solution) with a malabsorption syndrome (MAS) caused by Giardia lamblia.

Volunteer #1: Male, 28 years old. Type II MAS with positive isolation of Giardia lamblia in duodenal washings and confirmation of the disease by histopathology. The patient received metronidazole (Flagyl) during 7 days, having a good evolution. One month later, patient 1 presented symptoms and signs of recurrence of the disease, with positive isolation of parasites in feces. He received lidocaine intravenously twice a day during 2 days. Five days later, isolation of parasites in feces rendered negative results. Enteric histopathological examination revealed a type I MAS and D-xylose and Van der Kamer tests rendered normal values. Thirty days later, all tests performed revealed a normalization of enteric function with negative isolation of parasites.

Volunteer #2: Male, 36 years old, with diffuse abdominal pain, loss of body weight and steatorrhea. D-xylose and Van der Kamer tests, parasitologic analysis and enteric histopathological examination showed a type II MAS with positive isolation of Giardia lamblia.

Lidocaine was administered twice a day during 2 days by intravenous route (5 ml, 2% solution).

At day 7 post-treatment, the patient was asymptomatic, isolation of parasites rendered negative results, D-xylose and Van der Kamer tests were normal and microscopic examination of enteric mucosa revealed a type I MAS.

At day 28 post-treatment the patient remained asymptomatic, with gain of weight, normal tests, negative isolation of parasites and a normalization of the microscopic aspect of the enteric mucosa.

Conclusions: Lidocaine produces a favorable response in patients with MAS due to Giardia lamblia, eliminating the etiological agent and/or favoring a quick reinstallation of normal enteric function.

Example #5

Effects on the Evolution of Herpes Simplex Infection (Herpesvirus)

Ten volunteers with recidivant periorificial herpes simplex with a mean evolution of 6 months, of monthly eruption, who previously, during other episodes, received acyclovir (oral and/or topical), were incorporated to a schedule of treatment with lidocaine.

Patients were divided into 3 groups: one of the groups (n=4) received acyclovir by oral route and topical applications of the same drug. Another group (n=4) received lidocaine intra-venously (5 ml, 2% solution), and the third group (n=2) received lidocaine intravenously (5 ml, 2% solution) plus a topical and oral treatment with acyclovir. Experiments began with the appearance of the next episode of herpes, just in the moment when vesicles appeared.

Results: Group A (acyclovir alone): the episode begun with pain and erythema in the affected area. Next day, vesicle formation took place. At this moment, treatment was begun. Vesicles evolutionated with a tendency to coalesce, then, much of them broke, leaving a cruent base. At 48 hours a serohematic crust covered the ruptured vesicles. From the forth day, all vesicles were covered with crusts, but pain did not exist. Slowly, erythema tended to disappear, crusts begun to detach and by day 7 and almost complete reepithelization took place, with absence of signs and symptoms, remaining only a slight descamation of epidermis.

Group B (lidocaine): Patients presented similar symptoms and signs with respect to group A. At the moment that vesicles appeared, lidocaine was administered intravenously (twice a day during 2 days). Neither rupture of vesicles nor crust formation was found, and, by 48 hours after treatment was begun no pain existed and the injured area only presented a slight epidermal descamation.

Group C (lidocaine+acyclovir): In this group similar changes and evolution to group B were found.

|  | Number of Patients | Duration of symptoms | Duration of lesions |
| --- | --- | --- | --- |
| group A (ACV) | 4 | 4 days | 7 days |
| group B (lidocaine) | 4 | 2 days | 4.5 days |
| group C (lidocaine + ACV) | 2 | 2 days | 4.5 days |

All these patients were controlled monthly during the following 4 months. During this time, group A patients presented episodes with a pattern similar to that they had before the experiment was performed. On the other hand, 4 of 6 patients who received lidocaine did not present another episode of the disease. The remaining two presented an episode of herpes 2.8 and 3.3 months later. At the moment of the episode, they were treated with lidocaine, presenting an evolution similar to that previously was observed.

First Episode After Treatment:

| PATIENT NO.        | 1     | 2    | 3    | 4     | 5     | 6     |
|--------------------|-------|------|------|-------|-------|-------|
| GROUP A (ACV)      | 31 d. | 29 d | 33 d | 40 d. | —     | —     |
| GROUP B (lidocaine)| —     | —    | —    | —     | 84 d. | 94 d. |

Conclusions: Lidocaine was demonstrated to be highly effective in the treatment of herpetic episodes, reducing time of evolution and symptoms and signs. Also, it is effective as a preventive of recidives.

Example #6

Effects on the Course of Acute Viral A Hepatitis 4 male patients, 21 to 36 years old with clinical and serological diagnosis of acute viral A hepatitis were treated during symptomatic phase with lidocaine (5 ml, 2% solution) by intravenous administration (once a day during 7 days). Four other patients with similar characteristics were included in the schedule, but did not receive lidocaine.

Before administration of lidocaine bilirubin, cholesterol, glucose, LDH, GOT, CPK and prothrombin serum levels were measured. A week later the same determinations were performed and a physical examination was done in all patients.

Non-treated patients showed an evolution similar to that expected for the general population with this kind of hepatitis. Similarly, the biochemical parameters values were those expected.

On the contrary, lidocaine treated patients showed a surprising recovery, with good aspect, disappearance of jaundice in those 2 patients who presented it, absence of weakness and astenia, reduction of hepatomegalia and good tolerance to food. LDH, GOT, GPK, glucose and cholesterol values were among those considered normal. Bilirubin level decreased, but not to normal levels.

Conclusions: Lidocaine is effective in reducing signs and symptoms of acute viral A hepatitis, with a fast recovery of patients.

Example #7

Effects on Herpes Zoster Infection (Herpesvirus)

Three (3) patients with herpes zoster were included in an schedule of treatment with lidocaine.

PATIENT A: Male, 66 years old who presented a grade II vesical transitional carcinoma that was endoscopically resected. 60 days after resection he presented his first herpetic episode in chest, of 10 days of evolution. 175 days later, a second episode was presented, beginning with hyper and parastesy in the affected area and sudden appearance of vesicles. During this episode, lidocaine was administered by intravenous route (twice a day during 2 days) and evolution of the episode was evaluated.

After 48 hours of treatment, vesicles were covered by serohematic crusts, the erythematous skin tended to return to normality, the erythema disappearing 12 hrs. later. By day 5 post-treatment, pain did not longer exist and by day 7 crusts were detached spontaneously without sequelae.

PATIENT B: Female, 66 years old, without any apparent disease. 20 and 12 months before she presented two episodes of herpes zoster in the right submammary area, of high intensity, with exquisite pain that made impossible contact with clothes, each episode lasting 3 weeks. At the present time, the patient presented her third episode, preceded by fever (during 48 hours), with crusted vesicles, some of them impetiginized.

She received lidocaine intravenously (twice a day during 2 days) and topical oxytetracycline in some of the impetiginized vesicles, leaving others without topical treatment.

The lesion had a favorable evolution, with disappearance of pain and erythema 5 days after the treatment was begun. From day 10 post-treatment, all vesicles healed.

Topically treated impetiginized lesions showed an evolution similar to those non treated.

PATIENT C: Female, 57 years old, with a breast cancer, under chemo and hormone therapy. After each chemotherapy schedule received, she developed an herpetic episode in the left leg. During the last episode, she received lidocaine intravenously (twice a day during 2 days), showing an evolution of her herpetic lesions similar to those of the previous patients, but a residual hyperesthesia persisted.

Conclusions: the drug lidocaine is effective as a treatment in herpes zoster infection.

Example #8

Effects on Pancreatic Lesions Induced by Foot-and-Mouth Disease Virus (Picornaviridae)

Foot-and-mouth disease virus (FMDV) produces in mice an acute pancreatitis with recovery by a week of infection.

In order to know the effect of lidocaine on the evolution of pancreatitis in this animal model, the following experiments were performed:

Materials and Methods

Mice: 5 month-old male Swiss mice were used.

Virus: $O_1$ Caseros strain of FMDV was used.

Experimental schedule: Three (3) groups of animals were established:

Group A received lidocaine by endovenous route 24 hours after 100,000 pfu of FMDV were inoculated intraperitoneally. Group B only received FMDV, acting as a control group. Group C was simultaneously inoculated with FMDV and treated with lidocaine.

Two (2) mice of each group were sacrificed at 48, 72 and 96 hours post-infection, and the pancreas was removed for microscopic studies.

Results: Microscopic examination of pancreas of control group (B) showed a marked interstitial edema with polymorphonuclear leucocyte (PMN) infiltration and massive necrosis of acinar cells. From 72 hours post-infection (pi), the exocrine portion of the pancreas began to show a recovery of acinar cells, and by 96 hours post-infection no damage could be found.

Microscopic examination of the pancreas of groups A and C showed minimal inflammatory damage with absence of necrosis from 48 hours post-infection. At 72 hours post-infection no pancreatic damage could be found.

Conclusions: the drug lidocaine modifies the course of FMDV infection, reducing or abolishing pancreatic damage.

Comments: Similar experiments in which different dosages, administration routes and times of administration of lidocaine were used, showed similar results to that already described. Following Tables exemplify some of these results.

Effect on pancreas of different dosage of lidocaine administered by intramuscular route in Foot and Mouth Disease Virus (FMDV) infected mice (twice a day during 2 days). Animals received 0.1 ml of lidocaine in each administration in the dilutions named after the group name.

| GROUP NECROSIS | PRESENCE OF PMNs | PANCREATIC |
|---|---|---|
| A (0.8%) | 30–50% | 30–40% |
| B (0.4%) | 60–70% | 60–70% |
| C (0.2%) | 80–90% | 80–90% |
| D (control) | 100% | 90–100% |

Effect on pancreas of different dosages of lidocaine administered by intramuscular route previously (24 hours) to FMDV infection. Animals received 0.1 ml of a 0.8% solution of lidocaine twice a day before FMDV was administered.

| GROUP NECROSIS | PRESENCE OF PMNs | PANCREATIC |
|---|---|---|
| treated animals | 10% | 5–10% |
| control animals | 90–100% | 80–90% |

Effect on pancreas of different administration schedules in FMDV infection. Animals received 0.1 ml of lidocaine at different concentrations by intraperitoneal route.

Schedule

| GROUP | DOSAGE | 8 am (day 1) | 8 pm (day 1) | 8 am (day 2) | 8 pm (pi) (day 2) |
|---|---|---|---|---|---|
| A | 0.4% | + | – | – | – |
| B | 0.2% | + | – | – | – |
| C | 0.2% | + | + | – | – |
| D | 0.2% | + | + | + | – |
| E | 0.1% | + | + | – | – |
| F | 0.1% | + | + | + | + |
| G | control | – | – | – | – |

Results

| GROUP | PRESENCE OF PMNs | PANCREATIC NECROSIS |
|---|---|---|
| A | 10% | 5–10% |
| B | 60–70% | 30–50% |
| C | 30–40% | 10–20% |
| D | 30% | 10–20% |
| E | 80–90% | 40–60% |
| F | 10% | 5–10% |
| G (control) | 100% | 90–100% |

Effect on pancreas of different dosages of lidocaine in FMDV mice infection administered twice a day during 2 days by intramuscular route.

| GROUP | LIDOCAINE CONCENTRATION | PRESENCE OF PMNs | PANCREATIC NECROSIS |
|---|---|---|---|
| A | 0.1% | 50–60% | 20–30% |
| B | 0.2% | 20–30% | 5–10% |
| C | 0.3% | 10–20% | 0–5% |
| D | 0.4% | 10–20% | 0–5% |
| E | 0.5% | 10–20% | 0.5% |
| F | (control) | 100% | 80–90% |

Effect on pancreas of different dosages of lidocaine in FMDV mouse infection administered by oral route. An unique 2% solution of lidocaine was used, but varying the amount administered.

| GROUP | AMOUNT ADMINISTERED | PRESENCE OF PMNs | PANCREATIC NECROSIS |
|---|---|---|---|
| A | 0.1 ml | 50–100% | 50–100% |
| B | 0.2 ml | 30–60% | 80% |
| C | 0.3 ml | 30–60% | 60% |
| D | 0.4 ml | 50% | 40% |
| E | 0.5 ml. | 20–30% | 30% |
| F | control | 90–100% | 90–95% |

*animals received this treatment twice a day during 2 days.

Example #9

Effects in Acute Mercury Intoxication

In order to know the effects of lidocaine on mercuric dichloride ($HgCl_2$) intoxication, the following experiments were performed.

Material and Methods

Animals: 5 month-old female Swiss mice.

Toxic: Mercuric dichloride ($HgCl_2$) MW: 271.524

Experimental schedule: animals were divided in 6 groups:

Groups A and B received 0.5 mg. of $HgCl_2$ by intraperitoneal instillation, groups C and D received 1.0 mg of $HgCl_2$ by intraperitoneal route, and groups E and F received 2.0 mg of $HgCl_2$ by intraperitoneal route.

Groups A, C and E received Lidocaine by intraperitoneal administration twice a day during 2 days. The following Table summarized this schedule:

| Group | $HgCl_2$ | Lidocaine |
|---|---|---|
| A | 0.5 mg | + |
| B | 0.5 mg | – |
| C | 1.0 mg | + |
| D | 1.0 mg | – |
| E | 2.0 mg | + |
| F | 2.0 mg | – |

Surviving animals were sacrificed at 48 hours post-treatment and a necropsy was performed in the sacrificed animals and in those spontaneously dead. Samples of liver, bowel, pancreas, kidney and lung were removed for microscopic examination. Mortality was registered.

Results: Mortality:

Group F animals died 10 minutes after inoculation.

50% of group E animals died 10 minutes after inoculation, but the other half died 6 hours later.

50% of group D animals died 1 hour after inoculation and the other half died 12 hours post-inoculation.

Group C animals died between 12 and 24 hours post-inoculation.

Group B animals died 24 hours after inoculation.

Group A animals survived inoculation, being sacrificed 48 hours later.

Microscopic Examination

Group A: Generalized vascular congestion. No necrosis could be found;

Group B: Tubular renal necrosis. enteric villi necrosis, centrolobular hepatic necrosis, pancreatic acinar cell necrosis, Rupture and hemorrhages of alveolar walls;

Group C: Generalized vascular congestion. No necrosis could be found.

Groups D and E: The histological picture was similar to that of group B; and

Group F: Hepatocytic balloonization, hydropic degeneration of renal tubular cells.

Conclusions: The drug lidocaine can prevent necrosis in $HgCl_2$ acute intoxication when treated animals that receive 0.5 mg. of $HgCl_2$ survive intoxication. Higher doses of $HgCl_2$ produce death of animals, but treated ones showed less tissue damage.

The absence of necrosis in group F animals is attributed to the time animals survive intoxication (10 minutes).

Example #10

Effects in Acute Methanol Intoxication

In order to know the effects of lidocaine on acute methanol intoxication, the following experiment was carried out:

5 month-old male Swiss mice received either 0.1 or 0.2 ml of methanol by intraperitoneal route once a day during 2 days. Half of the animals received lidocaine by intraperitoneal administration twice a day during 2 days, accordingly with the following scheme:

| Group | Methanol | Lidocaine |
| --- | --- | --- |
| A | 0.1 ml | − |
| B | 0.1 ml | + |
| C | 0.2 ml | − |
| D | 0.2 ml | + |

A necropsy was performed in those animals spontaneously dead and in the surviving ones. Samples of liver, pancreas, kidney and lung were removed for microscopic examination.

Animals from group A showed immediately after inoculation of methanol an ataxia, which ceased in 30 min. This sign occurred again during the second administration of methanol.

Animals from group B showed no morbimortality.

Animals from group C showed immediately after inoculation of methanol an important ataxia. During the second administration of methanol animals showed ataxia again, and 50% of them died 4 hours later.

Animals from group D showed 30 minutes after methanol instillation an ataxia, but no deaths were found.

Microscopic Examination

Group A (without treatment): Scarce necrosis foci in liver, fatty degeneration and balloonization of hepatocytes. Acute necrotizing pancreatitis with affectation of 50% of the organ. Alveolar hemorrhages Group B (treated): Balloonization of hepatocytes. No necrotic and inflammatory damage could be found in organs examined.

Group C: Necrotic foci in liver which affected 50% of the parenchyma. Acute necrotizing pancreatitis with affectation of 70% of exocrine portion of pancreas. Massive alveolar hemorrhages. Renal tubular cortical necrosis.

Group D: Balloonization of hepatocytes. Scarce foci of alveolar hemorrhages.

Conclusions: lidocaine can prevent tissue damage produced by methanol intoxication.

Example #11

Effects of the Drug Lidocaine in Copper Sulfate Intoxication

In order to know the effects of lidocaine on copper sulfate intoxication the following experiment was designed.

5 month-old male Swiss mice received by intraperitoneal route 20 mg of copper sulphate ($CuSO_4$). Animals received 0.05, 0.1, 0.2 ml of lidocaine by oral route twice a day during 2 days. A necropsy was performed on sacrificed animals and on those spontaneously dead. Samples of liver, stomach, bowel, pancreas, kidney, spleen and lung were removed for microscopic examination. Morbimortality was checked each 12 hours. The scheme is showed in the following table:

| Group | $CuSo_4$ | Lidocaine |
| --- | --- | --- |
| A | + | 0.05 ml |
| B | + | 0.1 ml |
| C | + | 0.2 ml |
| D | + | — |

Results: Morbimortality:

From 48 hours post-administration of copper sulfate all animals of group D (non-treated) died. No mortality was found in the other groups. All animals of groups A, B and D presented a bluish coloration of skin and mucosa, being more intense in those of group D. Animals belonging to group C showed no bluish coloration.

Necropsy findings: Group D animals showed a bluish coloration in the walls of gastrointestinal tract, hepatomegalia and depletion of food in stomach. Such findings did not appear in other groups.

Microscopic Examination

Group A: Only minor balloonization of hepatocytes could be registered.

Group B: No alterations were found.

Group C: No alterations were found.

Group D: Mucosal necrosis of duodenum. Foci of hepatocytic balloonization.

Conclusions: The drug lidocaine is effective as a preventative of tissue damage produced by copper sulfate poisoning, so it also prevents lethality. The bluish coloration described herein can be attributed to sulphohemoglobinemia, which is prevented by lidocaine, depending of the dosage administered.

Example #12

Effects in Tissue Damage Produces in Mice by Mycoplasma Pneumoniae

Mycoplasmas cause an acute pneumonitis in human beings, generally affecting immune-depressed subjects, but also cause septicemia and pneumonia in cattle, with high mortality rates.

Since there exists an experimental model that reproduces lung lesions similar to those observed in man and cattle when infected with mycoplasmas, the following experiment was performed:

Materials and Methods

Animals: 5–7 month old male MPS mice were used.

Bacteria: Mycoplasma pneumoniae strains maintained in our laboratory were used.

Experimental schedule: all animals received by intranasal instillation 20 μl of a suspension of culture medium containing $10^7$ mycoplasmas, once a day during 4 days. Half of the animals received 0.1 ml of a 0.2% solution of lidocaine by intraperitoneal route twice a day during 4 days, beginning at the moment of bacteria instillation. Thereafter, animals received 0.2 ml of a 0.2% lidocaine solution once a day until experiment was finished. Animals were sacrificed at 10 days after the beginning of the infection and samples of lung were obtained for microscopic examination.

Results:

Group A animals (treated ones): scarce pneumonic foci, predominantly in a peribronchiollar distribution, composed of mononuclear cells, could be observed.

Group B animals (non-treated or control ones): a generalized pneumonia with mononuclear cells in alveolar walls and lumina with interstitial swelling could be observed.

Conclusions:

Lidocaine administration drastically modifies lung microscopic lesions, rendering in minor foci of pneumonia in treated animals as compared with control groups.

Example #13

Effect in Tissue Culture Viral Replication

Confluent monolayers of Vero (green monkey kidney cells) and $BHK_{21}$ (baby hamster kidney cells) cells were incubated during 1 hour at 37° C. in a 5% $CO_2$ atmosphere with a –3M solution of lidocaine. After two washings with RPMI culture medium, cell cultures were inoculated with 20 μl of RPMI medium containing $10^3$ $TCID_{50}$ of $O_1$ Caseros strain of Foot and Mouth Disease Virus (FMDV). Non treated cultures were inoculated in the same way and used as controls.

Results:

Results can be observed in the following table:

| Cells | Experimental | Control |
| --- | --- | --- |
| $BHK_{21}$ | $10^{4.5}$ $TCID_{50}$/ml | $10^{5.5}$ $TCID_{50}$/ml |
| VERO | $10^{3.5}$ $TCID_{50}$/ml | $10^{5.5}$ $TCID_{50}$/ml |

A similar experiment was performed in Vero and $BHK_{21}$ cells, either incubating cells with lidocaine and virus simultaneously or incubating cells with lidocaine 2 hours after adsorption has already occurred.

Results can be observed in the following table:

| Cells | Simultaneous Experimental | Treatment Control | Post-Adsorption | Experimental Control |
| --- | --- | --- | --- | --- |
| $BHK_{21}$ | $10^{4.3}$ | $10^{5.5}$ | $10^{5.5}$ | $10^{5.6}$ |
| VERO | $10^{3.6}$ | $10^{5.5}$ | $10^{5.6}$ | $10^{5.6}$ |

Viral titers are expressed as $TCID_{50}$/ml.

Conclusions:

Treated cultures rendered significantly lower titers when Vero cells were used, only when cultures were simultaneously treated or treated before viral adsorption takes place.

Similar experiments were performed using the same schedule, but changing the virus, using in these experiments Gumboro virus (a diplornavirus) and canine parvovirus (CPV).

Results:

Results can be observed in the following table:

| Cells | Virus | PRE-TREATMENT Exp. Control | SIMULTANEOUS T. Exp. Control | POST-TREATMENT Exp. Control |
| --- | --- | --- | --- | --- |
| $BHK_{21}$ | CPV | $10^{4.5}$ $10^{5.5}$ | $10^{4.5}$ $10^{5.6}$ | $10^{5.5}$ $10^{5.5}$ |
|  | Gumboro | $10^{2.5}$ $10^3$ | $10^{2.6}$ $10^3$ | $10^3$ $10^3$ |
| VERO | CPV | $10^{3.5}$ $10^{5.5}$ | $10^{3.6}$ $10^{5.5}$ | $10^{5.5}$ $10^{5.5}$ |
|  | Gumboro | $10^{3.5}$ $10^4$ | $10^{3.5}$ $10^4$ | $10^4$ $10^4$ |

Viral titers are expressed as $TCID_{50}$/ml.

Example #14

Effect in Cryptococcoses Produced in Experimentally Infected Mice

Materials and Methods

Animals: 5–7 month old female Swiss mice were used.

Experimental schedule: mice received by intraperitoneal route 0.5 ml of a suspension of $10^7$ Cryptococcus neoformans grown in Sabureaud medium. Half of the animals received 0.1 ml of a 0.2% solution of lidocaine by intraperitoneal route twice a day during 10 days.

Two animals of each group (experimental and control groups) were sacrificed at 2, 5 and 10 days post-infection and samples of liver, pancreas, brain, spleen, lung, kidney and bowel were obtained for microscopic examination.

In treated animals sacrificed at 48 hours post-infection (pi) one could observed only a generalized vascular congestion.

In control animals sacrificed at 48 hours pi, one could observed necrotic cells in liver with balloonization of hepatocytes, and a discrete acute pancreatitis with minor necrotic foci.

By 5 days post-infection it could be observed in treated animals a discrete mononuclear cell infiltrate in liver parenchyma and swelling of pancreatic tissue, with absence of inflammatory cells, and the presence of hepatic granulomas with hepatocyte necrosis, an acute necrotizing pancreatitis and only one granulomatous focus in brain (only in 1 animal) in control animals.

By day 10 pi it could be observed in treated animals scarce granulomas in hepatic parenchyma. The other organs showed no alterations with the exception of the spleen, where a follicular hyperplasia could be observed. On the contrary, non-treated animals showed many granulomatous foci in liver, pancreas, spleen and kidney, with some areas of necrosis in liver and pancreas and alveolar wall swelling.

Example #15

Effect in Histoplasmosis Produced in Experimentally Infected Mice

In a similar experiment as that described in Example #14, mice were infected with $10^7$ units of Histoplasma capsulatum. Animals were sacrificed at 5, 10 and 15 days post-infection (pi).

Results:

Results are summarized in the following table:

Treated Animals

|  | Day 5 pi | Day 10 pi | Day 15 pi |
|---|---|---|---|
| liver | small amount of necrosis | small amount of necrosis | small amount of granulomas |
| lung | no lesions | no lesions | granulomas |

-continued

|  | Day 5 pi | Day 10 pi | Day 15 pi |
|---|---|---|---|
| pancreas | no lesions | no lesions | no lesions |
| spleen | no lesions | small amount granulomas | small amount granuloma |
| kidney | no lesions | no lesions | no lesions |

Control Animals

|  | Day 5 pi | Day 10 pi | Day 15 pi. |
|---|---|---|---|
| liver | small amount of necrosis | granulomas | granulomas |
| lung | pneumonic foci | granulomas | granulomas |
| pancreas | minor pancreatitis | small amount granulomas | granulomas |
| spleen | small amount of lesions | small amount granulomas | granulomas |
| kidney | small amount lesions | small amount of lesions | small amount of lesions |

Example #16

Effect of Lidocaine on the Evolution of HIV (Retrovirus) Infected Patients

One group experiment conssited in 6 volunteer patients males and females aged between 22 and 35. Patient 1 (male 22 years old), patient 2 (female 30), patient 3 (male 27), and patient 4 (male 35) received Lidocaine by endovenous route, once a week. Patient 5 (male 25) and patient 6 (female 28), just received salline by same route and frequency as treated patients.

The evolution of the disease in the analyzed patients was done by counting the number of CD4+ cells/mm$^9$ blood and the CD4/CD8 ratio. Blood samples were collected every 15 days.

Results:

All the treated patients showed increase or no decrease in the CD4 counting and an increase or stability of the CD4/ CD8 ratio. The control patients experienced a decrease in the DC4 counting and in the CD4/CD8 ratio.

Patient 5 had recursive diarreas, hypoalbuminemia and a decrease in the number of platelets. The other patients showed sporadic episodes of disease.

By the end of the experiment no one of the analyzed patients died.

The table shows the number of CD4+ cells/mm$^9$ in blood samples obtained every 2 weeks. Treatment of patients started after the fourth sample extraction.

| patient | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1 | 400 | 475 | 475 | 480 | 480 | 480 | 485 | 490 | 495 | 500 | 500 | 505 | 510 | 520 | 530 |
| 2 | 294 | 294 | 280 | 270 | 280 | 298 | 300 | 295 | 300 | 305 | 302 | 305 | 310 | 310 | 314 |
| 3 | 230 | 238 | 235 | 234 | 238 | 234 | 238 | 238 | 238 | 238 | 240 | 242 | 244 | 242 | 242 |
| 4 | 500 | 496 | 496 | 485 | 490 | 490 | 492 | 496 | 496 | 496 | 496 | 498 | 500 | 500 | 498 |
| 5 | 522 | 507 | 461 | 439 | 416 | 393 | 370 | 360 | 343 | 333 | 324 | 311 | 295 | 281 | 267 |
| 6 | 300 | 298 | 293 | 292 | 289 | 286 | 279 | 263 | 252 | 239 | 235 | 224 | 218 | 213 | 210 |

Conclusions:

Lidocaine is effective in the treatment or at least in the status quo of the patients suffering from this retroviral infection.

What is claimed:

1. A method of providing a protective effect on plasma cell membranes in an animal in order to avoid cellular damage and to prevent the deleterious effect of diverse injuries caused by a viral infection or an immunodeficiency syndrome of non-viral etiology, the method comprising administering to the animal an effective amount of lidocaine hydrochloride (xylocaine) said amount provides a protective effect on plasma cell membranes, wherein said viral infection caused by a virus is selected from the group consisting of: rotavirus, parvovirus, enterovirus, rhinovirus, calicivirus, aphtovirus, coronavirus, papovavirus, adenovirus, viral hepatitis A, and infectious bursal disease virus (gumboro); and said immunodeficiency syndrome of non-viral etiology is acute hemorrhagic diarrhea.

2. A method according to claim 1, wherein the lidocaine hydrochloride is administered by intravenous administration.

3. A method according to claim 1, wherein the lidocaine hydrochloride is administered by intramuscular administration.

4. A method according to claim 1, wherein the lidocaine hydrochloride is administered by parenteral administration by an inhalation administration or by enteric administration.

5. A method according to claim 1, wherein the lidocaine hydrochloride is administered with vehicles for sustained release for parenteral administration.

6. A method according to claim 1, wherein the treated animal is suffering from rotavirus induced acute gastroenteropathies.

7. A method according to claim 1, wherein the treated animal is suffering from viral parvovirus infection.

8. A method according to claim 1, wherein the treated animal is suffering from enterovirus infection.

9. A method according to claim 1, wherein the treated animal is suffering from rhinovirus infection.

10. A method according to claim 1, wherein the treated animal is suffering from calicivirus infection.

11. A method according to claim 1, wherein the treated animal is suffering from aphtovirus infection.

12. A method according to claim 1, wherein the treated animal is suffering from equine abortion virus infection.

13. A method according to claim 1, wherein the treated animal is suffering from infectious laryngotracheitis virus infection.

14. A method according to claim 1, wherein the treated animal is suffering from Marek's Disease virus infection.

15. A method according to claim 1, wherein the treated animal is suffering from pseudorabies virus infection.

16. A method according to claim 1 wherein the treated animal is suffering from viral bursal Infectious Disease (gumboro).

17. A method according to claim 1, wherein the method provides a protective effect against structural damage and biochemical alterations on the plasma cell membrane.

18. A method according to claim 4, wherein the enteric administration is an oral or rectal route.

19. A method according to claim 4, wherein the parenteral administration is intrathecal, intraarticular, celomic or intraocular.

20. A method according to claim 5, wherein the parenteral administration is intravenous, subcutaneous, intramuscular, intrathecal, intraarticular, celomic or intraocular.

21. A method according to claim 5, wherein the vehicles are liposomes.

* * * * *